United States Patent [19]

Chatenever et al.

[11] Patent Number: 5,125,394
[45] Date of Patent: Jun. 30, 1992

[54] ENDOSCOPIC ADAPTER WITH LAMINA INTERFACE

[75] Inventors: David Chatenever, Santa Barbara; Daniel H. Mattsson-Boze, Goleta, both of Calif.

[73] Assignee: Medical Concepts, Inc., Goleta, Calif.

[21] Appl. No.: 621,574

[22] Filed: Dec. 3, 1990

[51] Int. Cl.⁵ .............................................. A61B 1/00
[52] U.S. Cl. ............................................ 128/4; 128/6
[58] Field of Search .................... 128/4, 6; 358/98

[56] References Cited

U.S. PATENT DOCUMENTS

| | | | |
|---|---|---|---|
| 4,439,030 | 3/1984 | Ueda | 354/62 |
| 4,611,888 | 9/1986 | Prenovitz et al. | 350/96.22 |
| 4,639,772 | 1/1987 | Sluyter et al. | 358/98 |
| 4,685,450 | 8/1987 | Collins et al. | 128/4 |
| 4,722,000 | 1/1988 | Chatenever | 358/98 |
| 4,756,304 | 7/1988 | Watanabe | 128/6 |
| 4,779,613 | 10/1988 | Hashiguchi et al. | 128/6 |
| 4,807,594 | 2/1989 | Chatenever | 128/4 |
| 4,844,071 | 7/1989 | Chen et al. | 128/6 |

Primary Examiner—John G. Weiss
Assistant Examiner—Cindy A. Cherichetti
Attorney, Agent, or Firm—Elliot N. Kramsky

[57] ABSTRACT

An adapter for an endoscopic system. An ocular piece is suitable for substitution for the eye-piece of a conventional endoscope. The ocular piece includes a window that is fitted into the end of a barrel-like member and slightly recessed from the edge thereof. The endoscope-engageable portion of the adapter includes a similar window that is also recessed creating a thin cavity therebetween. A latch mechanism at the end of the endoscope engageable portion of the adapter includes a plate having an interior circular aperture that can be selectively moved between positions that block and permit axial travel between the ocular piece and the endoscope engageable portion. The thin chamber between the windows is filled with sterilized water, preventing loss of optical clarity from the accumulation of liquid particles on window surfaces. The separtion between the windows permits rotation therebetween without damage to optical surfaces.

13 Claims, 2 Drawing Sheets

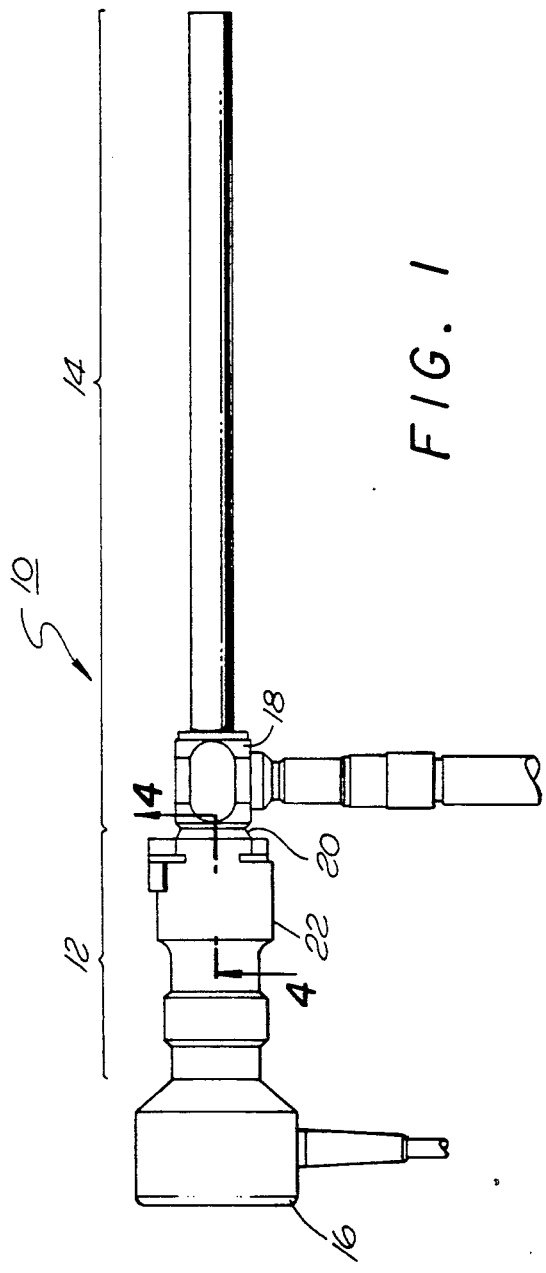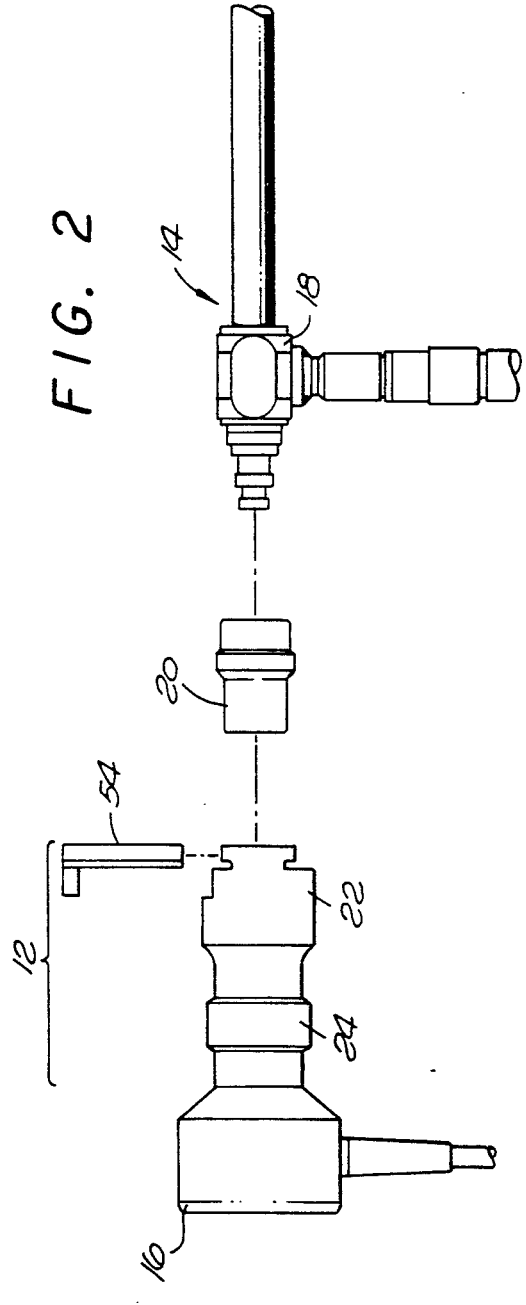

ENDOSCOPIC ADAPTER WITH LAMINA INTERFACE

BACKGROUND

1. Field of the Invention

The present invention relates to apparatus for coupling an endoscope to a camera head. More particularly, this invention pertains to an endoscopic adapter that includes an improved arrangement for coupling an endoscope to a video camera head that prevents fogging of optical elements during use.

2. Description of the Prior Art

The field of video endoscopy to which the present invention generally relates includes medical, diagnostic and therapeutic disciplines that utilize endoscopes to penetrate and view internal body cavities and organs with minimal intrusion and surgical procedures. Conventional endoscopes can generally be categorized as rigid or flexible and include, for example, the laparoscope, cystoscope, arthroscope, ureterscope, bronchoscope, and colonscope.

Video endoscopy has greatly enhanced the utility of endoscopic procedures. This technological advance requires apparatus for coupling the endoscope to the video camera head. Various couplers or endoscopic adapters generally include both real image forming optics and focusing apparatus mounted within a sleeve. Exemplary couplers and adapters are described in U.S. Pat. Nos. 4,076,018 of Heckele; No. 4,279,246 of Chikama; No. 4,344,092 of Miller; No. 4,413,278 of Feinbloom; No. 4,414,576 of Randmae; No. 4,439,030 of Veda; No. 4,621,618 of Omagari; and 4,639,772 of Sluyter, et al.; and Japanese Patent No. 58-21134 of Nishigaki.

Before use, the complete endoscopic system, including endoscope, adapter and video camera head must be disinfected by soaking or immersion in an appropriate solution, followed by rinsing in sterile water, drying and assembly. However, the viewing clarity of the adapter can often be hampered by the unavoidable trapping of residual liquid particles inside the various chambers formed between the conventional adapter and endoscope, as well as those between the adapter and the video camera head.

The endoscopic system is, therefore, vulnerable to liquid condensation at the adapter's optical surfaces. Condensation of the particles, which are heated by the heat emitted by the illumination source, generally occurs at the relatively cool front window of the optical adapter which offers a lower moisture-pressure gradient than the surrounding metal surfaces. The resulting reduction in clarity can significantly hinder the physician's diagnostic ability and his ability to perform surgical procedures.

While various techniques and couplers have been employed to minimize the condensation of residual fluid on the viewing optics, none has proven to be entirely satisfactory. One such coupler is described in U.S. Pat. No. 4,611,888 to Prenovitz, et al. While providing a compact coupler, this device suffers from drawbacks that render it less than desirable for modern applications. The Prenovitz et al. apparatus includes front and rear sections that are rotatable relative to one another to cause similar rotation of the endoscope relative to the camera head. The device further includes sealing means for reducing fogging.

The Prenovitz et al. coupler is, however, unsuitable for arthroscopic procedures that require use of multiple, interchangeable endoscopes since it requires soaking of the complete endoscopic system as a unit for disinfection. In fact, disconnection during the surgery can expose the image forming optics of the endoscopic system to contamination by fluids surrounding the surgical wound.

U.S. Pat. No. 4,807,594 of Chatenever teaches an endoscopic system that includes a "glass-on-glass" arrangement for maintaining optical clarity despite the presence of trapped liquid particles. The device of that patent essentially comprises a mechanism for creating a glass-on-glass interface between the endoscope and the adapter by the intimate contact between optical surfaces that does not permit intrusion of liquid particles therebetween. A glass-on-glass structure is achieved by removing the eyepiece of a conventional endoscope and replacing it with a so-called ocular adapter that comprises a tube-like structure with an optical window that engages the proximal end of the endoscope. The window is aligned axially with the optics of the endoscope and the camera head. It protrudes slightly from the back wall of the ocular adapter toward an opposed window in the wall of the endoscope engageable portion of the adapter.

While providing an advantageous arrangement that is particularly useful for situations or procedures requiring more than one interchangeable endoscope, the glass-on-glass structure suffers numerous drawbacks. Particular care must be take to avoid scratching of the contacting optical windows. This requires, in part, a relatively-complex mechanical arrangement for moving the optical adapter into engagement with the endoscope engageable portion. Such a mechanism is required to control the purely axial interengagement of the two windows to avoid the potential scratching that can result from rotational motion between contacting windows. Further, the windows of the glass-on-glass device are necessarily formed of very hard, scratch-resistant (and expensive) materials such as sapphire. Finally, as it is often required to rotate the axis of the endoscope with respect to that of the camera head, the adapter-to-camera head mounting must permit rotation as rotation cannot occur between the endoscope and the adapter for the reasons discussed above.

SUMMARY OF THE INVENTION

The present invention addresses the foregoing and other shortcomings of the prior art by providing an improvement in an endoscopic adapter of the type that includes an elongated adapter body having opposed ends. The first end of such an adapter body is arranged to engage a camera head while the second end is arranged to engage an endoscope. The improvement includes an ocular piece. Means are provided for fixing the ocular piece to the proximal end of the endoscope. The ocular piece includes a first substantially planar window while the second end of the adapter includes a second substantially planar window. The ocular piece and the second end of the endoscope are arranged so that the first and second windows are substantially aligned along the axis of the adapter. The first window is recessed into the ocular piece and the second window is recessed into the second end to define a cavity therebetween.

BRIEF DESCRIPTION OF THE DRAWINGS

The above-mentioned and other objects and features of the present invention and the manner of obtaining them will become apparent, and the invention itself will be best understood, by reference to the following description of the embodiment of the invention, taken in conjunction with the accompanying drawings, wherein:

FIG. 1 is an elevation view of an endoscopic system in accordance with the invention;

FIG. 2 is an exploded elevation view of an endoscopic system in accordance with the invention;

DETAILED DESCRIPTION

Figure 3:
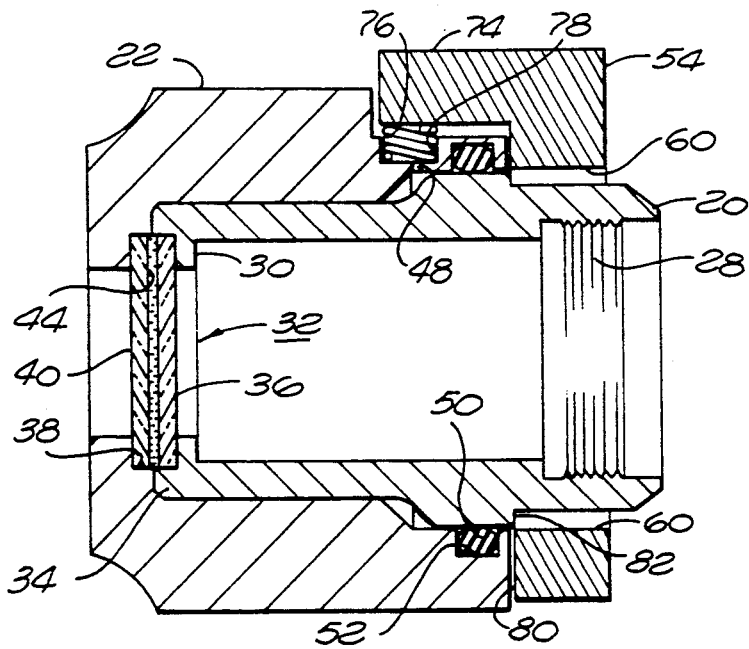
FIG. 3 is a cross-sectional elevation view of the ocular piece and endoscopic engageable portion of the adapter taken at line 3—3 of FIG. 4.

FIG. 1 is an elevation view of an endoscopic system in accordance with the invention and FIG. 2 is an exploded elevation view thereof. The system 10 includes an adapter assembly 12 for coupling an endoscope 14 and a video camera head 16. As shown, the assembly 12 is integral with the camera head 16. However, the invention is not so limited and may be practiced with a removable adapter-to-camera head assembly. The endoscope 14 may be one of any number of conventional types, either rigid or flexible in nature.

The proximal end of the endoscope 14 terminates in a hub 18 for interconnecting the endoscope to the adapter assembly 12 and to the required illumination source. The endoscope 14 produces a virtual image of the internal body region probed that is then processed and focused by the optics of the adapter assembly 12 and transmitted to an electronic pick-up device (e.g. a CCD imager) within the camera head 16.

An eyepiece is generally fixed to the hub 18 at the proximal end of the endoscope 14. However, similar to the adapter of U.S. Pat. No. 4,807,594 discussed above, in the present invention an ocular piece 20 replaces the eyepiece of the "standard" endoscope. This minor modification to an otherwise "off the shelf" instrument may be accomplished at either the point of manufacture or through simple and straightforward modifications (Note: since the endoscope is a costly precision instrument, this type of modification should be referred to a facility possessing the proper, specialized tooling and should not be attempted ordinarily by the practicing physician.)

In the present invention, the adapter 12 including the ocular piece 20 functions in a way that is both analogous and superior to that of the adapter systems that incorporate or utilize the function of a conventional endoscope eyepiece. Further, the invention achieves substantial advantages over the previously-referenced "non-eyepiece" device that employs glass-on-glass technology.

The adapter assembly 12 shown in FIG. 1 can be rigidly fixed to the camera head 16. Rotation of the endoscope relative to the camera is often required. Numerous endoscope types "look" at an angle with respect to the optical axis of the shaft or probe and must be rotated to provide the physician with a comprehensive view of the operating area. In the present invention, such rotation is not limited to the interface between adapter 12 and camera head 16.

The adapter 12 also includes an endoscope engageable portion 22, described in greater detail below, and a conventional focusing ring 24 that is rotatable with respect to the adapter 12 for controlling the axial positioning of focusing optics therein.

In use, the eyepiece of the conventional endoscope 14 is detached (if necessary) and the ocular piece 20 then threadedly attached to the hub 18. Prior to use, the camera head 16, the adapter 12 and the endoscope with ocular eyepiece 20 may be separately disinfected and soaked in sterile water. The endoscope-engageable portion 22 of the adapter assembly 12 is then easily secured to the ocular piece 20 by a latching means (discussed below). Once the adapter assembly 12 is coupled to the endoscope 14 (and to the attached camera head 16) the system is configured for medical use. Furthermore, other endoscopes, each with an ocular piece fixed to its proximal hub, may readily be substituted during a single medical procedure without complication or loss of visual clarity.

Figure 4:
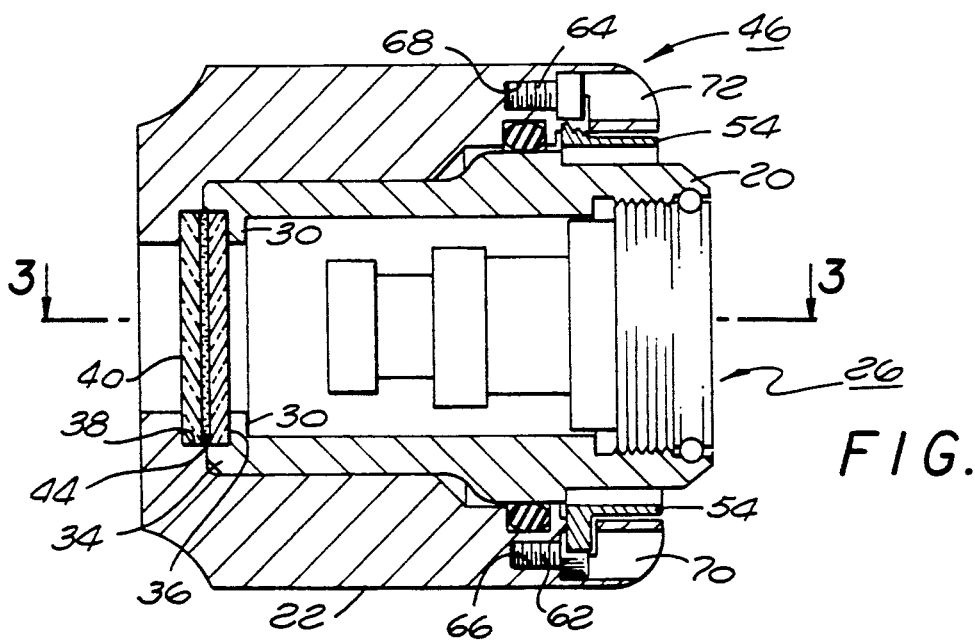
FIG. 4 is a cross sectional top plan view of the ocular piece and endoscope engageable portion of the adapter taken at line 4—4 of FIG. 1.

FIG. 3 is a cross-sectional elevation view of the ocular piece 20 and endoscope engageable portion 22 of the adapter 12 taken at line 3—3 of FIG. 4 and FIG. 4 is a top plan view of the same arrangement in cross-section taken at line 4—4 of that figure. The content of FIG. 4 differs from that of FIG. 3 by display of a portion of the proximal hub 18 of the endoscope 14. However, as the most proximal portion of the hub 18 comprises a symmetrical threaded structure 26, little is lost by omitting this element from FIG. 3 and, of course, additional clarity is gained.

The ocular piece 20 comprises a generally tube-like body that includes an interiorly threaded portion 28 for engaging the exteriorly threaded structure 26 of the proximal hub 18. The substantially permanent attachment is strengthened by an appropriate bonding agent. Thus, the ocular piece 20 effectively replaces the eyepiece of the endoscope with a device that is compatible with the other teachings of this invention. The ocular piece is designed to mate with the proximal hub of a standard endoscope. Accordingly numerous endoscope sizes, shapes and types can be modified by means of a single type of ocular piece. As will be seen, an appropriately modified endoscope can be readily fixed to and removed from the adapter 12. That is, the interior of the tube-like ocular piece 20 is designed for conformance to the geometry of a standard hub 18 while the exterior of the ocular piece 20 is designed for compatibility with the endoscope engageable portion 22.

The body of the ocular piece 20 is preferably formed of stainless steel machined to a tolerance of ±0.0005 inches. In cases where electrical isolation of the endoscope from the adapter is required, this ocular piece may be formed out of an insulating material such as that marketed under the trademark "LEXAN". The rear of the tube-like body terminates in an annular wall 30 having a central aperture 32 that is orthogonal to the optical axis of the endoscope 12. The body of the piece 20 terminates in an inwardly protruding flange 34 that provides a region for receiving a window 36 of optical quality glass. The window 36 is secured within the annular flange 34 by an appropriate adhesive.

A small recess is maintained between the rear surface of the window 36 and that of the ocular piece 20. This recess results from the fact that the depth of the flange 34 exceeds the thickness of the window 36. A similar recess is created by the relative depth of an annular shoulder 38 that is positioned at the rear of the endoscope engageable portion 22 for mounting a window 40. By arranging metal bearing surfaces and separating the windows 36 and 40 from each other, a distance of on the order of 0.010 to 0.015 inches is maintained between adjacent surfaces of the windows 36 and 40, creating a thin chamber 44.

The chamber 44 may be either "dry" or filled with sterilized fluid. In either case, since the optical windows 36 and 40 are separated, significant shortcomings of the glass-on-glass arrangement of the prior art are overcome. The absence of intimate contact between the windows 36 and 40 eliminates the potential for scratching of optical surfaces caused by rotation therebetween. From this it follows that, among other advantages, (1) the windows need not be restricted to extremely hard (and expensive) materials, (2) rotation can occur between the ocular piece 20 and the endoscope engageable portion 22, thereby enlarging options for design of the overall endoscopic system and (3) a complex mechanical assembly (or any means for that matter) is not required to assure purely axial movement between the two optical windows during engagement of the adapter to the endoscope.

The interface can be operated "dry" if there are no required substitutions of endoscopes and if the separable components of the endoscopic system are completely dried prior to assembly. Substitution of endoscopes necessitates the operation of the interface with a liquid lamina layer.

After soaking, the engagement of the "wet" endoscope to the adapter is attained by pointing the adapter 12 upwardly to trap sterilized water and then inserting the ocular piece (with attached endoscope, of course) downwardly until it is latched into place as shown in FIGS. 3 and 4. (A latch mechanism 46, discussed below, permits the ready attachment and detachment of the ocular piece 20 and the endoscope engageable portion 22.)

A small hole 48 (about 0.05 inch diameter) in the stainless steel body of the barrel-like portion 22 permits evacuation of air and excess liquid from the mated devices, leaving a uniform lamina layer of sterilized water to fill the chamber 44. An O-ring 50 seated within an internal circumferential bore 52 of the portion 22 provides rotational resistance. The close tolerance provided between the ocular piece 20 and the endoscope engageable portion 22 (between 0.0005 inch and 0.0015 inch) acts to retain the liquid layer through the effect of capillary action.

The lamina layer allows rotation without abrasion of the opposed surfaces of the windows 36 and 40. The bearing surfaces of the ocular piece 20 and the endoscope engageable portion 22 are of stainless steel. Since the cavity 44 is completely filled with water, fogging cannot result from condensation of trapped liquid particles on the window surfaces.

Figure 5:
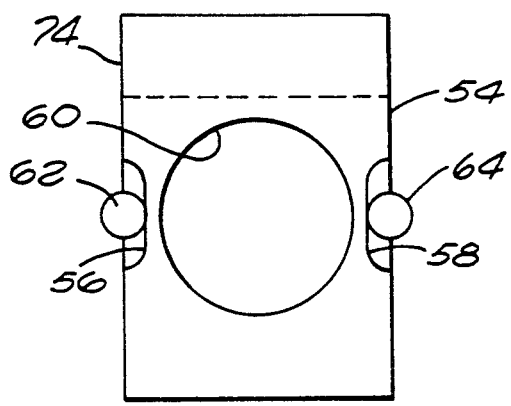
FIG. 5 is a front elevation view of the latch plate of the invention.

FIG. 5 is a front elevation view of the latch plate 54 of the invention for releasably securing adapter and endoscope. As shown, opposed, elongated lateral cutouts 56 and 58 are formed at either side of a central circular cutout 60 of the plate 54. As can be seen in FIGS. 3 and 4, the cutout 60 encircles the ocular piece 20, its diameter exceeding the outer diameter of the barrel-like ocular piece 20 to permit clearance therebetween. Such clearance allows the latch plate 54 to be moved between positions that lock and unlock the endoscope engageable portion 22 of the adapter to the endoscope 14.

Referring now to FIG. 4 in conjunction with FIG. 5, screws 62 and 64 are symmetrically displaced in the horizontal plane and threadedly engaged to counterbored regions 66 and 68 of the endoscope engageable portion 22 respectively. The heads of the screws 62 and 64 protrude into access holes 70 and 72 machined into the body of the endoscope engageable portion 22, forming stop positions of the latch plate 54 ("locked" and "unlocked") in the vertical plane.

Referring to FIG. 4, a cantilevered flange 74 adjoins the top of the latch plate 54 and points toward the camera head end of the adapter 12. The flange 74 overlies and abuts a spring 76 seated within a bore 78 in the endoscope engageable portion 22. When compressed, the spring 76 exerts an upwardly-directed force upon the bottom of the flange 74, raising the latch plate 54 to an extent that is limited only by abutment of the inwardly-curved bottom edges of the cutouts 56 and 58 with the heads of the screws 62 and 64. At the same time, the inner edge 80 of the latch plate 54 adjacent the central cutout 60 abuts the lower annular ridge 82 of the ocular piece 20, securely locking it (and the endoscope 14) to the endoscope engageable portion 22 of the adapter 12.

The orientation of the latch plate 54 for unlocking the endoscope 14 from the endoscope engageable portion 22 is shown in FIG. 4. Unlocking is accomplished by depressing the flange 74, (preferably with the thumb). This compresses the spring 76 and lowers the latch plate 54 until the inwardly-curved upper edges of the cutouts 56 and 58 abut the screws 62 and 64. When this occurs, the internal circular aperture 60 is aligned with the ocular adapter 20 as shown in FIG. 4.

As shown, when the flange 74 is depressed the aperture 60 is aligned with the ocular piece 20 in such a way that the annular inner surface 80 of the latch plate 54 no longer abuts the annular ridge 82 of the ocular piece 20. Consequently, when the flange 74 is depressed axial movement of the ocular piece 20 relative to the endoscope engageable portion 22 is entirely unrestricted and the endoscope 14 can be easily removed from or inserted into the adapter 12. Thus, the latching mechanism provides the physician with a simple, ergonomic means for ready substitution of endoscopes during medical procedures.

Thus, it is shown that the present invention provides an extremely useful new instrument for use in adapting endoscopy to video technology. Accordingly, the invention enhances the attractiveness and utility of this increasingly helpful medical technology. By utilizing the teachings of this invention, the physician is enabled to perform procedures that require the substitution of multiple endoscopes without encountering many of the problems and limitations experienced in the past. Furthermore, the invention possesses excellent optical transmission qualities. A simple and relatively inexpensive anti-reflection coating such as magnesium fluoride is subject to only 0.2 percent glass-to-water reflection which is quite superior to the measured performance of glass-on-glass interfaces that experience reflection on the order of 2 to 4 percent.

The apparatus of the invention is extremely ergonomic, providing a flange-button demanding little dexterity on the part of the physician for locking and unlocking of endoscopes made interchangeable by the invention. The lamina layer between the windows of the ocular piece and the adapter provides lubrication that brings a greater amount of freedom to overall endoscopic system design. Relative rotation can take place between the adapter and the endoscope without abrasion of optical surfaces. Furthermore, expensive materials are not mandated for the windows of the ocular piece and the adapter and the mechanical linkages therebetween are substantially simplified.

While this invention has been described with respect to its presently preferred embodiment, it is not limited thereto. Rather, this invention is limited only insofar as defined by the following set of claims and includes all equivalents thereof within its scope.

What is claimed is:

1. In an endoscopic adapter of the type that includes an elongated adapter body having opposed ends, a first end being arranged to engage a camera head and a second end being arranged to engage an endoscope, the improvement comprising, in combination:
   a) an ocular piece;
   b) a chamber member having opposed open and closed ends for receiving said ocular piece;
   c) means for fixing said ocular piece to the proximal end of said endoscope;
   d) said piece including a first substantially planar window located at an end thereof adjacent said closed end of said chamber member;
   e) said chamber member including a second substantially planar window;
   f) said first and second windows being substantially aligned along the optical axis of said adapter; and
   g) said first window being recessed into said ocular piece and said second window being recessed into said closed end of said chamber member to define a substantially planar cavity therebetween.

2. An adapter as defined in claim 1 further including means for releasably fixing said adapter to said endoscope.

3. An adapter as defined in claim 2 further characterized in that:
   a) said ocular piece is generally cylindrical; and
   b) said chamber member is generally-cylindrical.

4. An adapter as defined in claim 3 wherein said means for releasably fixing additionally includes:
   a) a latch plate;
   b) said plate being located at the chamber member; and
   c) means for selectively moving said plate between two predetermined positions so that said endoscope may be alternately locked to and removable from said adapter.

5. An adapter as defined in claim 4 further characterized in that:
   a) said latch plate includes an internal aperture;
   b) said plate is arranged so that said aperture surrounds said ocular piece;
   c) said ocular piece includes an annular ridge; and
   d) said means for selectively moving said plate includes means for moving said plate between a position that abuts said annular ridge and a position wherein said ocular piece is unimpeded by said plate.

6. An adapter as defined in claim 5 wherein said means for selectively moving said plate is further characterized in that:
   a) said plate includes an integral horizontal flange; and
   b) a spring is located between said the chamber member and said flange for urging said latch plate to said locking position.

7. An adapter as defined in claim 6 wherein said means for selectively moving said plate is further characterized in that:
   a) said plate includes a pair of opposed elongated edge cutouts; and
   b) means are arranged within said cutouts for defining the limits to movement of said latch plate.

8. An adapter as defined in claim 7 wherein said last-named means comprises a pair of screws affixed to said chamber member.

9. An adapter as defined in claim 8 wherein said camera head is fixed to said first end of said adapter so that rotational movement is not permitted therebetween.

10. An adapter as defined in claim 8 further including an O-ring for providing rotational friction between said ocular piece and said adapter.

11. An adapter as defined in claim 10 including a pressure release hole in said chamber member.

12. An adapter as defined in claim 11 wherein said pressure release hole is located in said sealed interface between said ocular piece and said chamber member.

13. An adapter as defined in claim 1 wherein said cavity is filled with liquid.

* * * * *